(12) United States Patent
Butler et al.

(10) Patent No.: US 11,439,442 B2
(45) Date of Patent: Sep. 13, 2022

(54) MODULAR SCREW SYSTEM WITH HEAD LOCKER AND DEROTATOR

(71) Applicant: Warsaw Orthopedic, Inc., Warsaw, IN (US)

(72) Inventors: Brian A. Butler, Atoka, TN (US); Molly K. Rice, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 85 days.

(21) Appl. No.: 16/850,385

(22) Filed: Apr. 16, 2020

(65) Prior Publication Data
US 2021/0322067 A1    Oct. 21, 2021

(51) Int. Cl.
*A61B 17/70* (2006.01)
*A61B 17/02* (2006.01)
*A61B 17/00* (2006.01)

(52) U.S. Cl.
CPC ........ *A61B 17/7082* (2013.01); *A61B 17/708* (2013.01); *A61B 17/7035* (2013.01); *A61B 17/7032* (2013.01); *A61B 2017/00464* (2013.01); *A61B 2017/0256* (2013.01)

(58) Field of Classification Search
CPC ........................................ A61B 17/7074–7092
See application file for complete search history.

(56) References Cited

U.S. PATENT DOCUMENTS

| 6,530,929 | B1 | 3/2003 | Justis et al. |
| 6,565,568 | B1 | 5/2003 | Rogozinski |
| 7,670,358 | B2 | 3/2010 | Barry |
| 7,749,233 | B2 | 7/2010 | Farr et al. |
| 7,776,072 | B2 | 8/2010 | Barry |
| 7,951,168 | B2 | 5/2011 | Chao et al. |
| 7,951,175 | B2 | 5/2011 | Chao et al. |
| 8,007,516 | B2 | 8/2011 | Chao et al. |
| 8,038,699 | B2 | 10/2011 | Cohen et al. |

(Continued)

OTHER PUBLICATIONS

"CD Horizon Solera 5.5/6.0 Spinal System, Surgical Technique," www.medtronic.com<http://www.medtronic.com>, Medtronic Inc., copyright 2014.

(Continued)

*Primary Examiner* — Eduardo C Robert
*Assistant Examiner* — Steven J Cotroneo
(74) *Attorney, Agent, or Firm* — Fox Rothschild LLP; P. Marshall Ticer

(57) ABSTRACT

A universal surgical instrument includes an elongated member having a first end and a second end, the second end having flexible prongs with a head cavity to hold therebetween a polyaxial head. The universal surgical instrument includes a cuff member at the first end to interface with interchangeable surgical instruments. The universal surgical instrument includes an I-shaped clamp coupled to the elongated member and being configured to unlock and separate the flexible prongs to expand the head cavity for placement of the polyaxial head therein and to lock the head cavity in response to application of a force to slide the I-shaped claim along the elongated member to a locked position. A system of surgical instruments include the universal instrument and interchangeable surgical instruments that can be interchanged in the cuff member of the universal instrument.

14 Claims, 16 Drawing Sheets

(56) References Cited

U.S. PATENT DOCUMENTS

| | | | |
|---|---|---|---|
| 8,162,952 B2* | 4/2012 | Cohen | A61B 17/708 606/104 |
| 8,187,334 B2 | 5/2012 | Curran et al. | |
| 8,211,110 B1 | 7/2012 | Corin et al. | |
| 8,394,109 B2* | 3/2013 | Hutton | A61B 17/708 606/105 |
| 8,535,318 B2 | 9/2013 | Peterson et al. | |
| 8,591,515 B2* | 11/2013 | Jackson | A61B 17/7082 606/86 A |
| 8,623,022 B2 | 1/2014 | Forton et al. | |
| 8,709,044 B2 | 4/2014 | Chao et al. | |
| 8,795,283 B2 | 8/2014 | Petit | |
| 8,821,502 B2 | 9/2014 | Gleeson et al. | |
| 8,845,649 B2 | 9/2014 | Jackson | |
| 8,876,835 B2 | 11/2014 | Petit | |
| 8,900,240 B2 | 12/2014 | White et al. | |
| 8,906,034 B2 | 12/2014 | Gleeson et al. | |
| 8,936,605 B2 | 1/2015 | Greenberg | |
| 9,011,447 B2* | 4/2015 | Arnett | A61B 17/8863 606/86 A |
| 9,125,694 B2 | 9/2015 | Butler et al. | |
| 9,155,573 B2* | 10/2015 | May | A61B 17/7077 |
| 9,179,957 B2 | 11/2015 | Ibrahim et al. | |
| 9,241,742 B2 | 1/2016 | Stad | |
| 9,271,767 B2 | 3/2016 | Jackson | |
| 9,314,273 B2 | 4/2016 | Iott et al. | |
| 9,314,280 B2 | 4/2016 | Corin | |
| 9,320,550 B2 | 4/2016 | Hutton et al. | |
| 9,351,770 B2 | 5/2016 | Sharps | |
| 9,402,662 B2 | 8/2016 | Mahar | |
| 9,402,663 B2 | 8/2016 | Peterson et al. | |
| 9,480,500 B2 | 11/2016 | Ibrahim et al. | |
| 9,480,504 B1 | 11/2016 | Schafer et al. | |
| 9,510,875 B2 | 12/2016 | Reitblat et al. | |
| 9,532,815 B2 | 1/2017 | Jackson | |
| 9,603,628 B2 | 3/2017 | Butler et al. | |
| 9,629,667 B2 | 4/2017 | Petit | |
| 9,642,654 B2 | 5/2017 | Reimels et al. | |
| 9,668,776 B2 | 6/2017 | Ibrahim et al. | |
| 9,808,281 B2 | 11/2017 | Solitario, Jr. et al. | |
| 9,877,750 B2 | 1/2018 | Iott et al. | |
| 9,936,986 B2 | 4/2018 | Butler et al. | |
| 9,968,384 B2 | 5/2018 | Fischer et al. | |
| 9,999,448 B2 | 6/2018 | Stad | |
| 10,028,773 B2 | 7/2018 | Ibrahim et al. | |
| 10,034,695 B1 | 7/2018 | Schafer et al. | |
| 10,052,140 B2 | 8/2018 | Krause et al. | |
| 10,085,807 B2 | 10/2018 | Butters et al. | |
| 10,219,845 B2 | 3/2019 | Petit | |
| 10,258,390 B2 | 4/2019 | Biedermann et al. | |
| 10,314,624 B2 | 6/2019 | Chao et al. | |
| 10,441,328 B2 | 10/2019 | Petit | |
| 10,499,952 B2 | 12/2019 | Iott et al. | |
| 10,568,669 B2 | 2/2020 | Reitblat et al. | |
| 10,595,912 B2 | 3/2020 | Krause et al. | |
| 2003/0065328 A1 | 4/2003 | Shevtsov et al. | |
| 2005/0085813 A1 | 4/2005 | Spitler et al. | |
| 2005/0245928 A1 | 11/2005 | Colleran et al. | |
| 2008/0015601 A1 | 1/2008 | Castro et al. | |
| 2008/0077134 A1* | 3/2008 | Dziedzic | A61B 17/7076 606/86 A |
| 2010/0004695 A1* | 1/2010 | Stad | A61B 17/7074 606/86 A |
| 2011/0166606 A1* | 7/2011 | Stihl | A61B 17/7091 606/279 |
| 2012/0265212 A1* | 10/2012 | Seck | A61B 17/708 606/102 |
| 2013/0012999 A1* | 1/2013 | Petit | A61B 17/7076 606/279 |
| 2013/0018419 A1* | 1/2013 | Rezach | A61B 17/7076 606/264 |
| 2013/0184763 A1* | 7/2013 | McClintock | A61B 17/7077 606/279 |
| 2013/0211453 A1* | 8/2013 | Lenke | A61B 17/7077 606/250 |
| 2014/0188182 A1 | 7/2014 | Chao et al. | |
| 2014/0277200 A1* | 9/2014 | Parker | A61B 17/7037 606/86 A |
| 2015/0051648 A1* | 2/2015 | May | A61B 17/7086 606/264 |
| 2015/0164569 A1* | 6/2015 | Reitblat | A61B 17/7079 606/279 |
| 2016/0310174 A1 | 10/2016 | Peterson et al. | |
| 2017/0049428 A1* | 2/2017 | Cryder | A61B 17/86 |
| 2017/0079696 A1 | 3/2017 | Walker et al. | |
| 2017/0112551 A1 | 4/2017 | Suh et al. | |
| 2017/0311980 A1 | 11/2017 | Solitario, Jr. et al. | |
| 2018/0185072 A1 | 7/2018 | Rubin et al. | |
| 2018/0235676 A1 | 8/2018 | Butler et al. | |
| 2019/0008565 A1 | 1/2019 | Peterson et al. | |
| 2019/0021772 A1 | 1/2019 | Schafer et al. | |
| 2019/0090908 A1 | 3/2019 | Stad | |
| 2019/0142471 A1 | 5/2019 | Lindner | |
| 2019/0307492 A1 | 10/2019 | Chao et al. | |
| 2019/0336182 A1 | 11/2019 | Suh et al. | |
| 2020/0069338 A1 | 3/2020 | Iott et al. | |
| 2020/0305932 A1 | 10/2020 | Park | |

OTHER PUBLICATIONS

"Deformity Procedural Solutions, AIS Procedural Solutions," www.medtronic.com<http://www.medtronic.com>, Medtronic Inc., copyright 2018.

Olerud et al.. Transpedicular Fixation of Thoracolumbar Vertebral Fractures, Clinical Orthopaedics and Related Research 227:44-51 (1988).

* cited by examiner

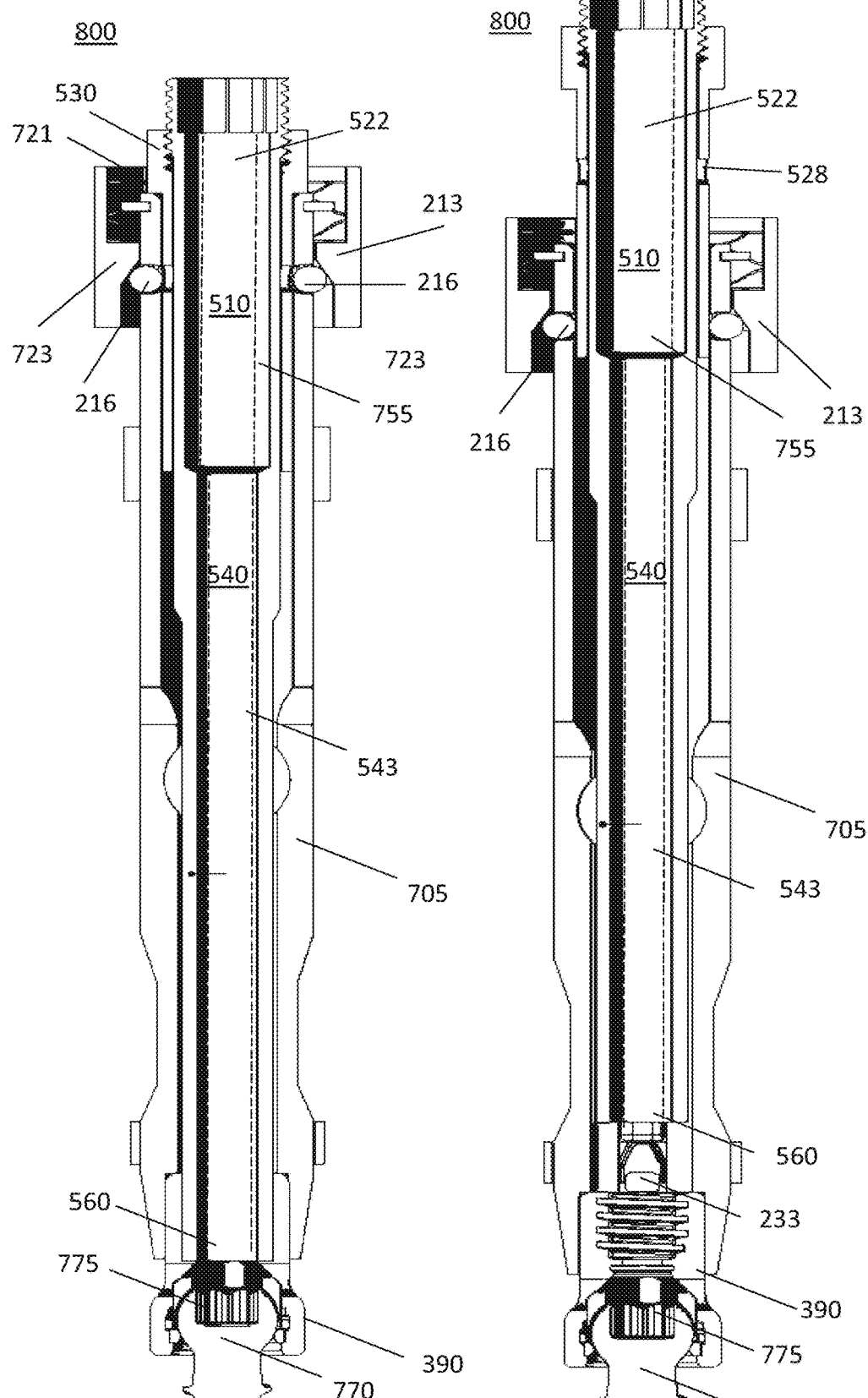

MODULAR SCREW SYSTEM WITH HEAD LOCKER AND DEROTATOR

FIELD

The present technology is generally related to a universal modular instrument that may be used for various tasks depending upon the module to incorporate into the instrument, such as, connecting portions of a screw system, for locking the head on a screw, or for various other uses such as connection of multiple instruments for derotation or for compression or distraction.

BACKGROUND

With a screw fastening system, the polyaxial head should be attached to the bone screw, which means an instrument may be attached to the screw head and then the instrument removed and another different instrument attached to, for example, do correction maneuvers with the screw. This can increase the number of times one or more instruments are attached to the head such as to perform different functions to adjust or correct the screw.

SUMMARY

The techniques of this disclosure generally relate to a universal and easy attachment portal to allow different interchangeable surgical instruments to be interchanged during surgery to decrease the amount of time the surgeon spends connection/disconnecting instrumentation.

In one aspect, the present disclosure provides a universal surgical instrument that includes an elongated member having a first end and a second end, the second end having flexible prongs with a head cavity to hold therebetween a polyaxial head. The universal surgical instrument includes a cuff member at the first end to interface with interchangeable surgical instruments. The universal surgical instrument includes an I-shaped clamp coupled to the elongated member and being configured to unlock and separate the flexible prongs to expand the head cavity for placement of the polyaxial head therein and to lock the head cavity in response to application of a force to slide the I-shaped claim along the elongated member to a locked position.

In another aspect, the disclosure provides a surgical instrument system comprising at least one universal surgical instrument. Each universal surgical instrument includes an elongated member having a first end and a second end. The second end has flexible prongs with a head cavity to hold therebetween a polyaxial head. Each universal surgical instrument includes a female attachment channel at the first end, and an I-shaped clamp coupled to the elongated member and being configured to unlock and separate the flexible prongs to expand the head cavity for placement of the polyaxial head therein and to lock the head cavity in response to application of a force to slide the I-shaped claim along the elongated member to a locked position. The system includes at least one interchangeable surgical instrument. Each interchangeable surgical instrument includes a male attachment interface to mate with the female attachment channel, the male interface prevents rotation in the female attachment channel.

In another aspect, the disclosure provides an interchangeable surgical instrument including a surgical device configured to perform a surgical function, the surgical device having an instrument body. The interchangeable surgical instrument includes at least one male interface integrated in the instrument body to mate with a female attachment channel of a universal instrument, the male interface prevents rotation in the female attachment channel The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 8A is a cross-sectional view of a system with the universal instrument having the first interchangeable surgical instrument at a fifth partially inserted position in the universal instrument and with the knob turned to an intermediate position to push the crown and lowered in the collar.

FIG. 8B is a cross-sectional view of a system of FIG. 8A with the universal instrument having the first interchangeable surgical instrument being in a retracted position relative to the universal instrument.

DETAILED DESCRIPTION

Figure 1:
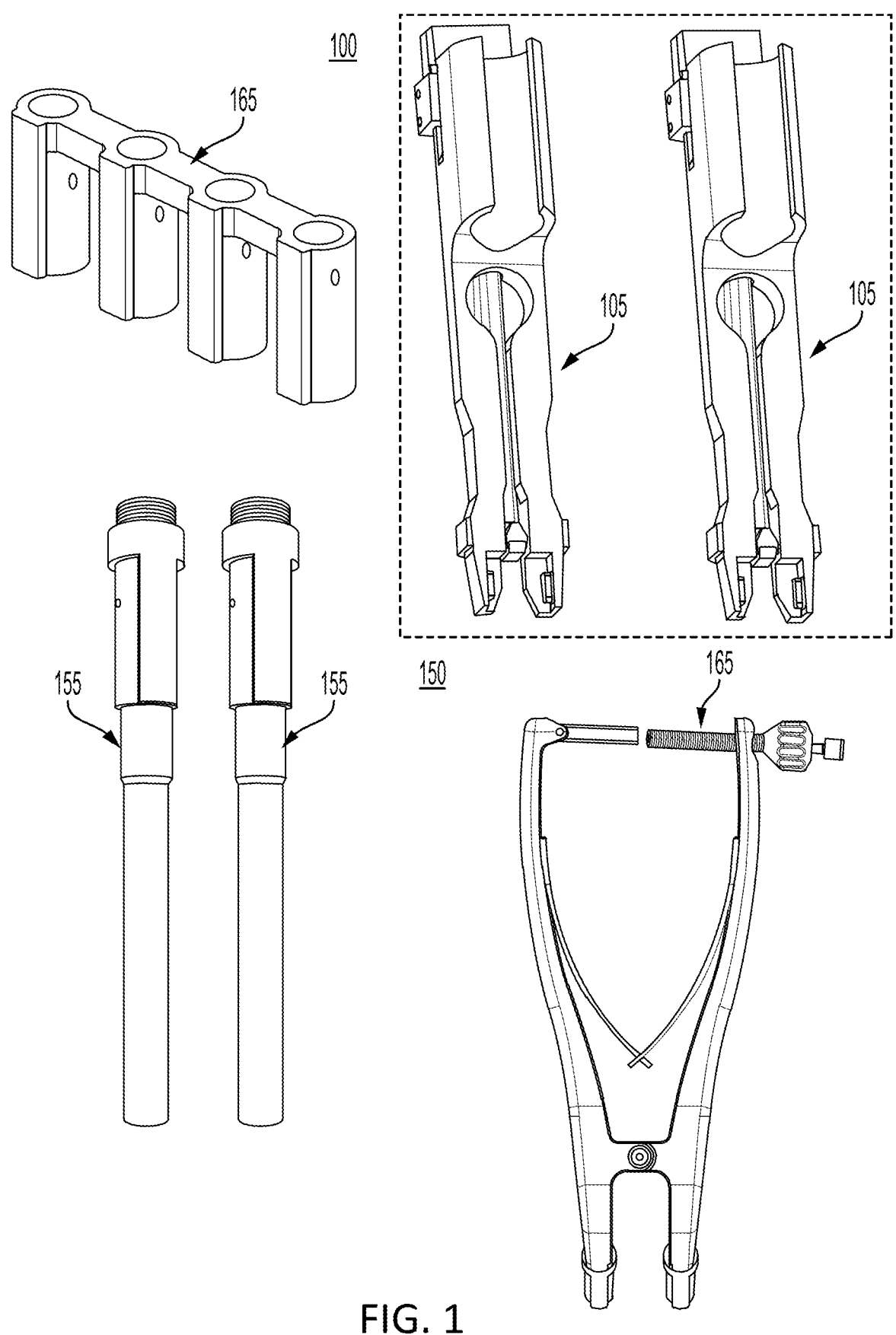
FIG. 1 is a perspective view of components of a modular universal surgical system with principles of the present disclosure.

The embodiments of a surgical system are discussed in terms of medical devices for the treatment of musculoskeletal disorders and more particularly, in terms of a surgical system and a method for treating a spine. In some embodiments, the system includes a universal instrument and interchangeable surgical instruments mated to the universal instrument and related methods of use that can be employed with spinal constructs including bone fasteners and connectors having a pop on, snap on, click on and/or slide on member that provides a universal connection system to spine surgeons. In some embodiments, the spinal construct allows the use of a singular bone screw component with a universal instrument and interchangeable surgical instruments thereby minimizing inventory while creating assemblies customized for a specific patient.

The system of the present disclosure may be understood more readily by reference to the following detailed description of the embodiments taken in connection with the accompanying drawing figures that form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, front, back, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIG. 1, components of a modular surgical implant system 100 are illustrated, in accordance with the principles of the disclosure.

The components of system 100 can be fabricated from biologically acceptable materials suitable for medical applications, including metals, synthetic polymers, ceramics and bone material and/or their composites. For example, the components of system 100, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologic Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of system 100 may have material composites, including the above materials, to achieve various desired characteristics such as strength, rigidity, elasticity, compliance, biomechanical performance, durability and radiolucency or imaging preference. The components of system 100, individually or collectively, may also be fabricated from a heterogeneous material such as a combination of two or more of the above-described materials. The components of system 100 may be monolithically formed, integrally connected or include fastening elements and/or instruments, as described herein.

The system 100 may include at least one surgical instrument 155 and is employed, for example, with an open or mini-open, minimal access and/or minimally invasive including percutaneous surgical technique to deliver and fasten an implant at a surgical site within a body of a patient, for example, a section of a spine. In one embodiment, the components of system 100 are configured to fix a bone fastener, such as a pedicle screw, with tissue for a surgical treatment to treat various spine pathologies, such as those described herein.

Figure 3B:
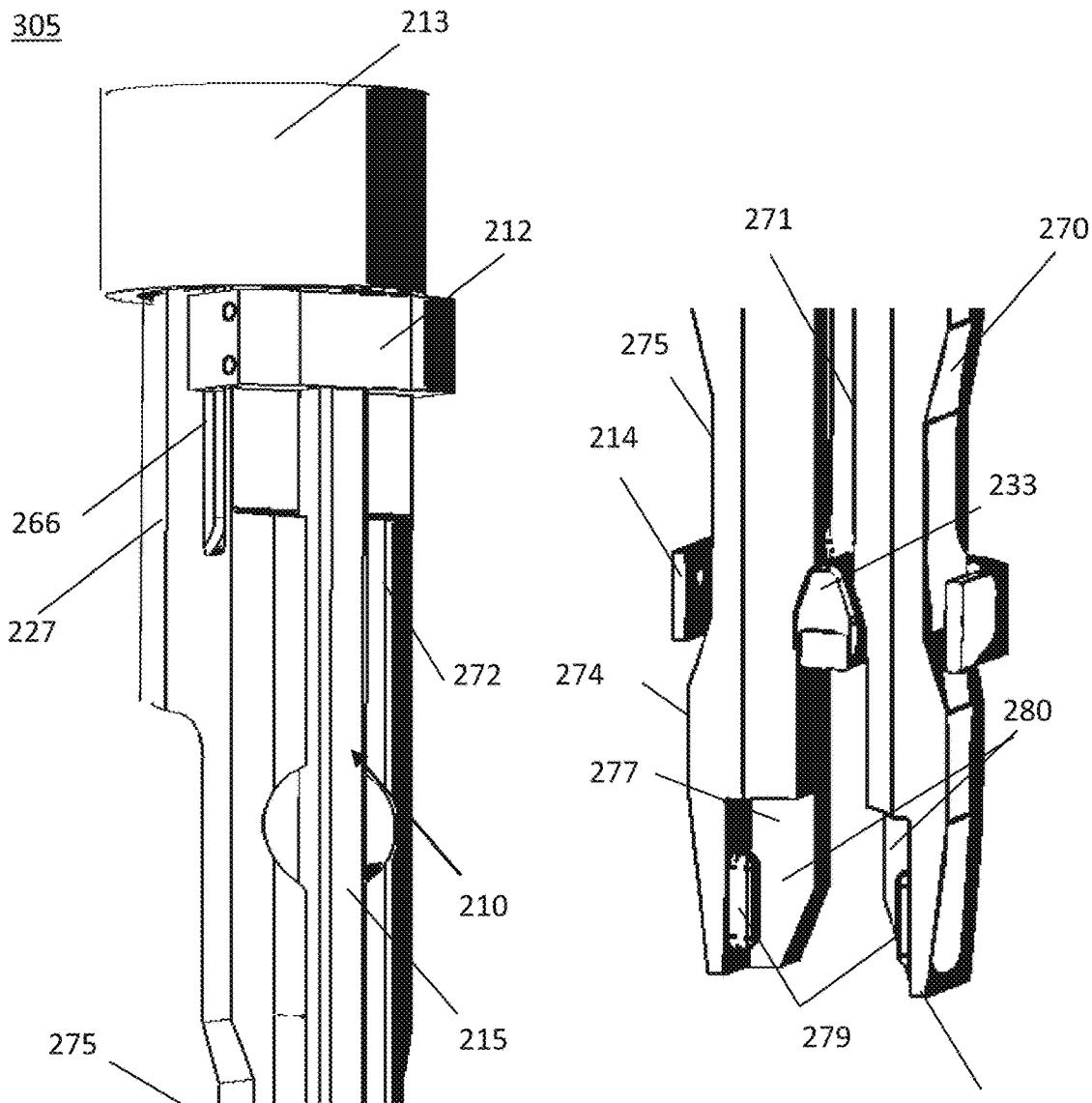
FIG. 3B is a partial view of the universal instrument of along the plane 3B of FIG. 2B.
Figure 3A:
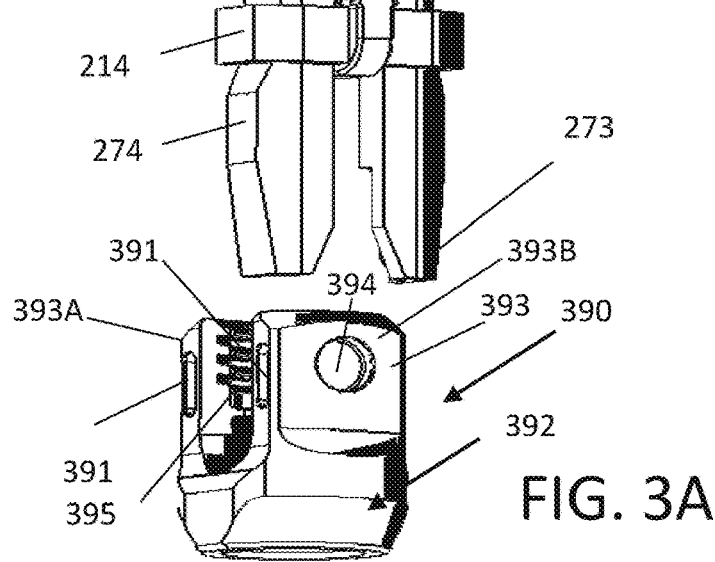
FIG. 3A is a perspective view of the universal instrument and a polyaxial head.

FIG. 1 is a perspective view of components of a modular universal surgical system 100 with principles of the disclosure. The modular feature of the surgical system 100 decreases the number of times an instrument may be attached to the polyaxial head 390 (FIG. 3A). In a scenario, the system 100 may include at least one universal instrument 105 and a plurality of interchangeable surgical accessories 150. A plurality of universal instruments 105 are set off in a dashed box with the interchangeable surgical accessories 150 remaining outside of the dashed box. By way of non-limiting example, the interchangeable surgical accessories 150 may include a first surgical accessory 155, a second surgical accessory 165 and a third surgical accessory 175.

By way of non-limiting example, first surgical accessory 155 may be configured as a head locker instrument. After the bone screw is in position, the head locker instrument 155 locks the polyaxial head 390 (FIG. 3A) to the bone screw such as by pushing the crown down. The head locker instrument 155 pushes an upper ring 765 (FIG. 7C and 7D) into an expansion chamber, preventing the lower ring from entering that chamber. Furthermore, others accessories could be used for rod reduction, compression, or distraction. For example, a second surgical accessory 165 may include a compressor/distractor instrument, as will be described in more detail in relation to FIGS. 9A-9B. Still further, the third surgical accessory 175 may be used as a crosslink to allow multiple universal instruments 105 to be connected for derotation, as will be described in more detail in relation to FIG. 10. The three accessory instruments described herein are example, instruments for use with the system. Other accessory instruments for a surgical treatment to treat various spine pathologies may be used and modified with a mated male attachment interface, as described herein.

Having an easy attachment mechanism to allow different functions may also decrease the amount of time the surgeon spends connection/disconnecting instrumentation. The polyaxial head may be configured with a base that allows a pedicle screw or other bone anchor to have a range of motion along several different axes.

The system 100 may include a plurality of universal instruments 105, each of which may be used for attaching to a different polyaxial head for a pedicle screw only once. Then, interchangeable surgical accessories may be interchanged during surgery to perform other functions by attaching an interchangeable surgical accessory to the universal instrument 105 while the universal instrument is locked or clamped onto the polyaxial head.

With the modular universal surgical system 100, the polyaxial head 390 may be attached to the bone screw, which means the universal instrument 105 may remain attached to the polyaxial head 390. Thereafter, the head locker instrument 155 may then be removed to do any correction maneuver with the screw, if necessary. The modular feature of the system 100 allows different interchangeable surgical accessories to perform different functions throughout the medical procedure.

Figure 2A:
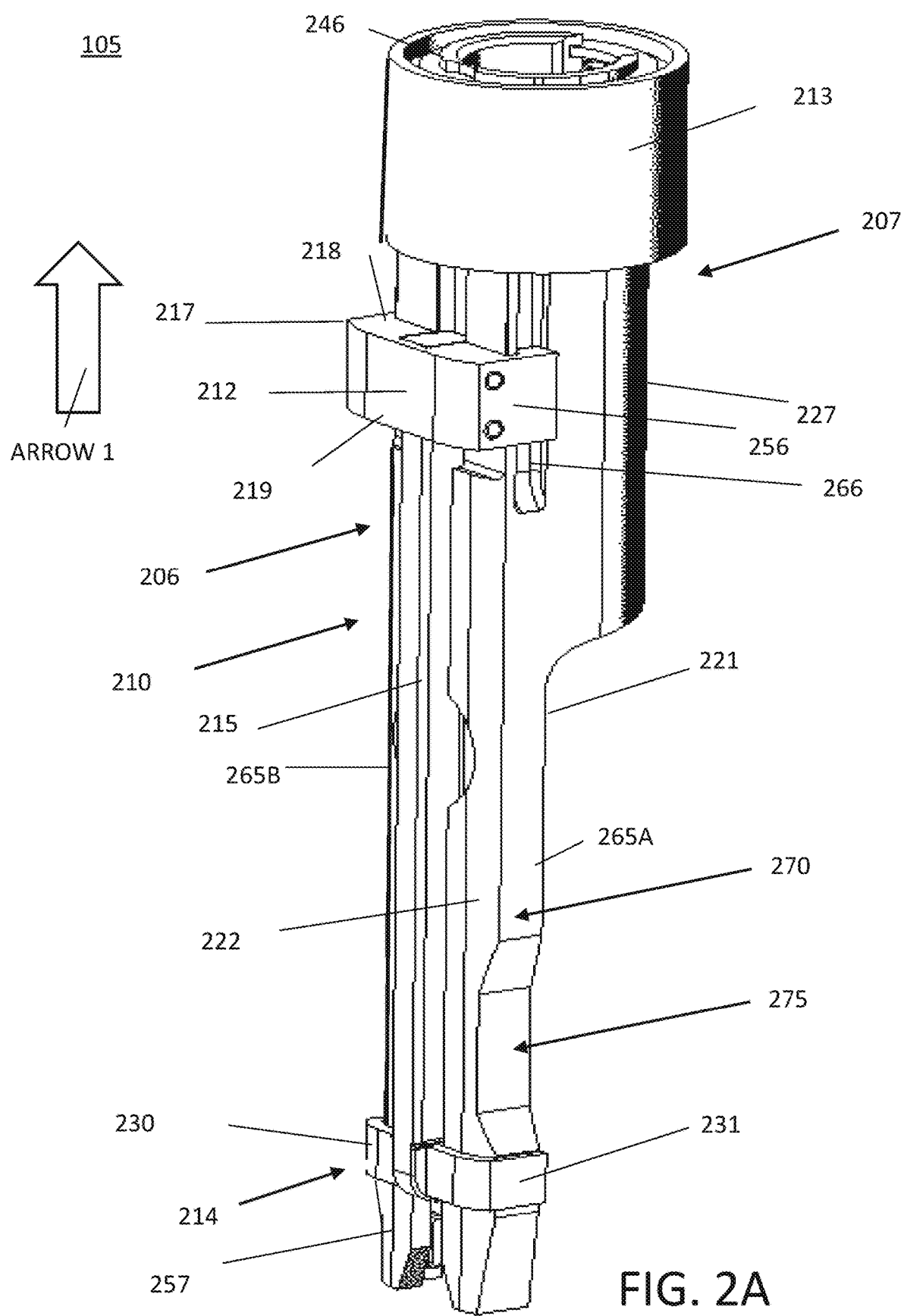
FIG. 2A is a first (rear) side perspective view of a universal instrument in FIG. 1.
Figure 2B:
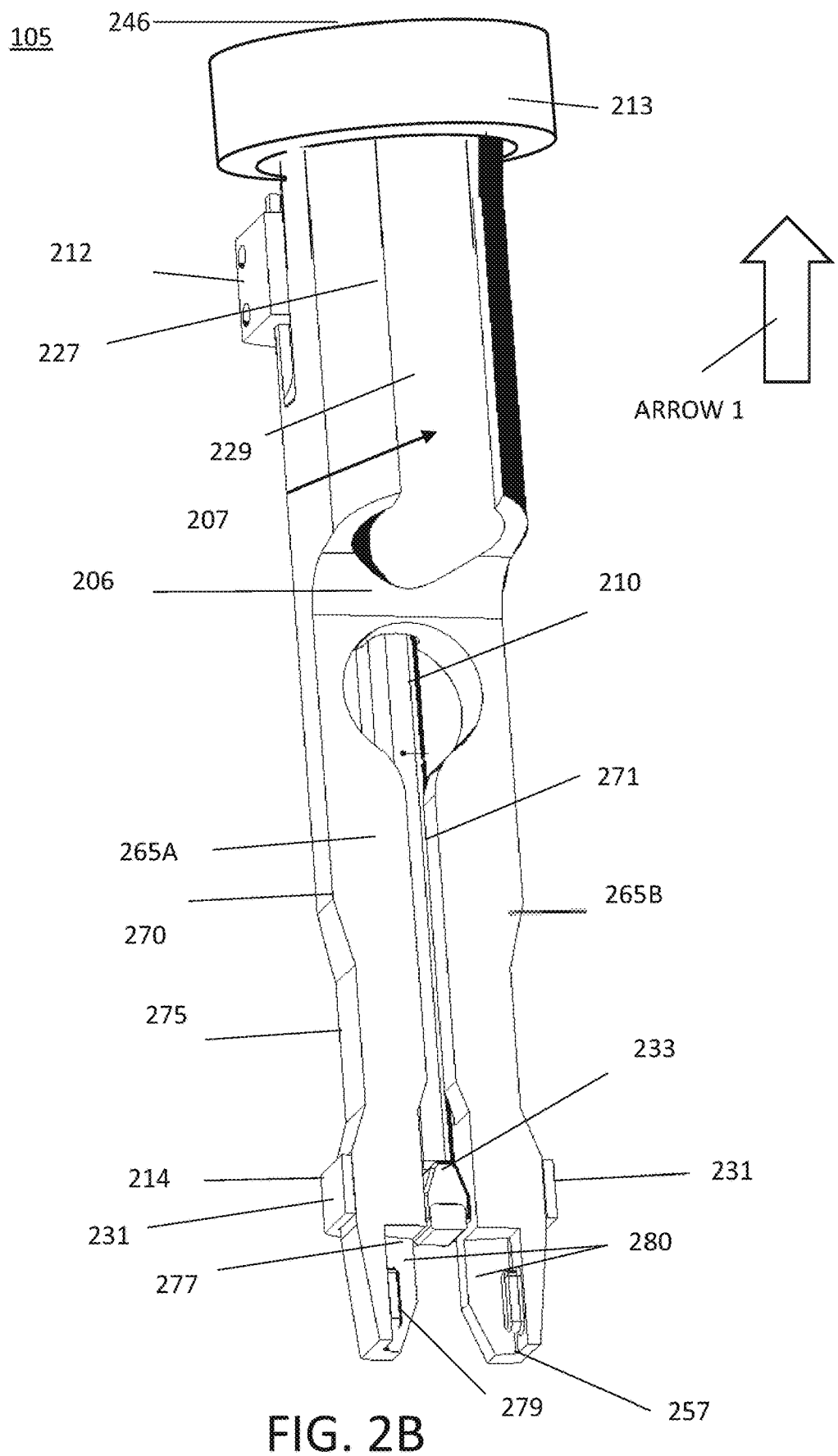
FIG. 2B is a second (front) side perspective view of a universal instrument of the components in FIG. 1.
Figure 2C:
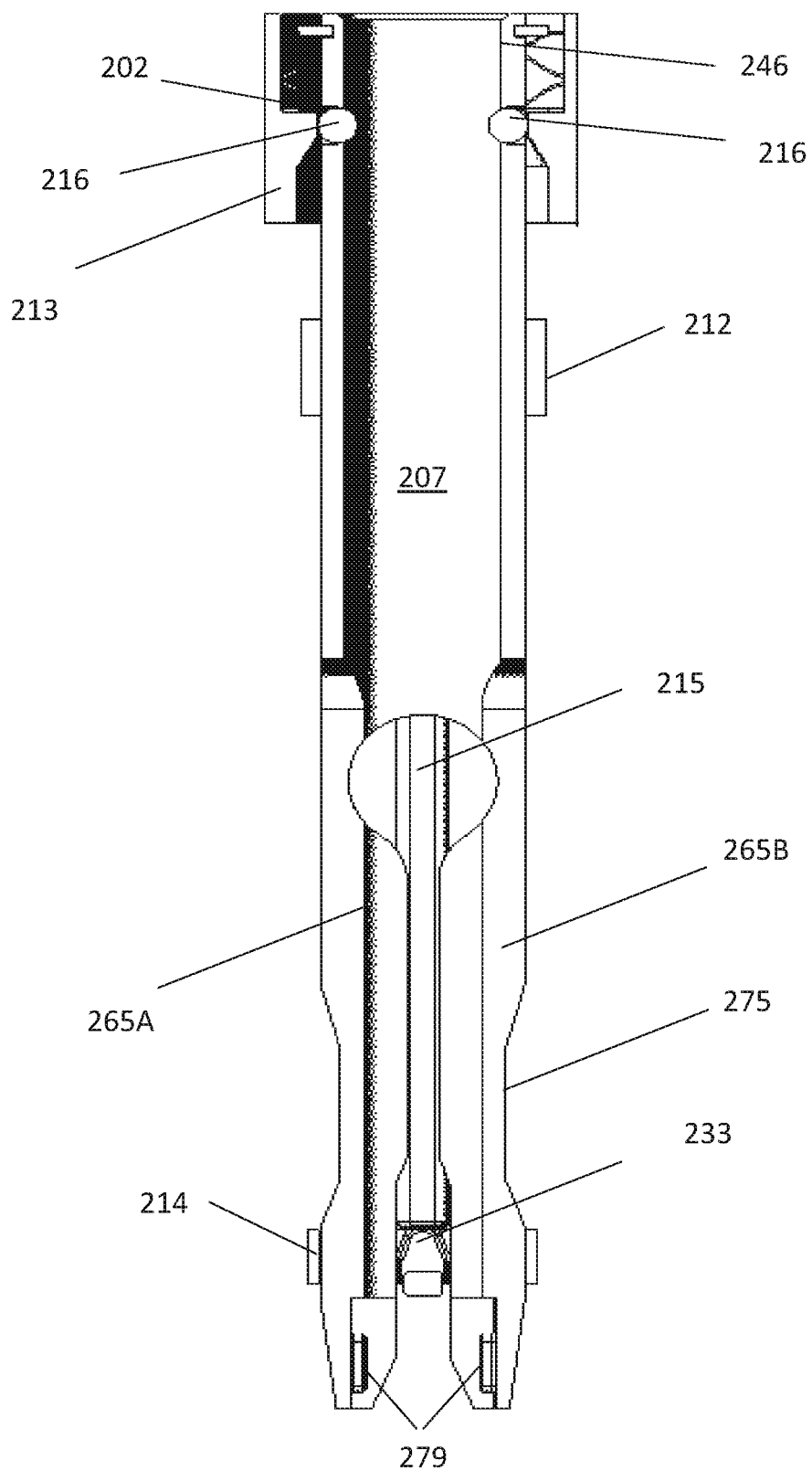
FIG. 2C is a cross-sectional view of the universal instrument of the components of FIG. 1

FIG. 2A is a first (rear) side perspective view of a universal instrument 105 FIG. 1. FIG. 2B is a second (front) side perspective view of a universal instrument of the components in FIG. 1. The universal instrument 105 may include an elongated member 206 having a first end 246 and a second end 257. The second end may have flexible prongs 265A and 265B to hold therebetween a polyaxial head 390, as best seen in FIG. 3A. FIG. 2C is a cross-sectional view of a universal instrument of the components in FIG. 1. The collar 213 of the universal instrument 105 includes ball detents 216 which are configured to fit in apertures 202 formed in opposing sides of the female attachment channel 207. The ball detents 216 are to secure one or more of the interchangeable instruments. The description of the ball detents will be described in more detail in relation to FIGS. 7A-7D.

The universal surgical instrument 105 may include a female attachment channel 207. The female attachment channel 207 may be configured to interface with interchangeable secondary instruments with mated male attachment interfaces 510 (FIG. 5A), 910 (FIG. 9B) and 1010 (FIG. 10) by way of non-limiting example. Each secondary instrument includes an instrument body having at least one mated male attachment interface.

The first end 246 of the elongated member 206 is an extension which extends above the clamp member 212. The length of the first end 246 allows a collar 213 to be installed above the clamp member 212. The collar 213 include a mechanism (i.e., ball detents 216) to lock interchangeable surgical instruments to the universal surgical instrument 105.

The universal surgical instrument 105 may include an I-shaped clamp 210 slidably coupled to the elongated member 206. The I-shaped clamp 210 may include a first clamp member 212 slidably coupled to or in close proximity to the first end 246 of the elongated member 206 and a second clamp member 214 slidably coupled in proximity to the second end 257. The I-shaped clamp 210 may include an interconnecting bar 215 interconnecting the first clamp member 212 to the second clamp member 214.

The I-shaped clamp 210 may further include a wedge 233 coupled to the second clamp member 214. The second clamp member 214 may have a C-shape including a cross bar 230 and two dependent sides 231. The wedge 233 may be positioned in a middle of the cross bar 230. The wedge 233 of the I-shaped clamp 210 may be positioned between the flexible prongs 265A and 265B so that as the I-shaped clamp 210 may be slid from a first position to a second position, the cross bar 230 follows in the direction of force. As the second clamp member 214 slides up, the wedge 233 may be, for example, between the flexible prongs 265A and 265B. A distance between the flexible prongs 265A and 265B expands by application of a force by the wedge 233.

Figure 4A:
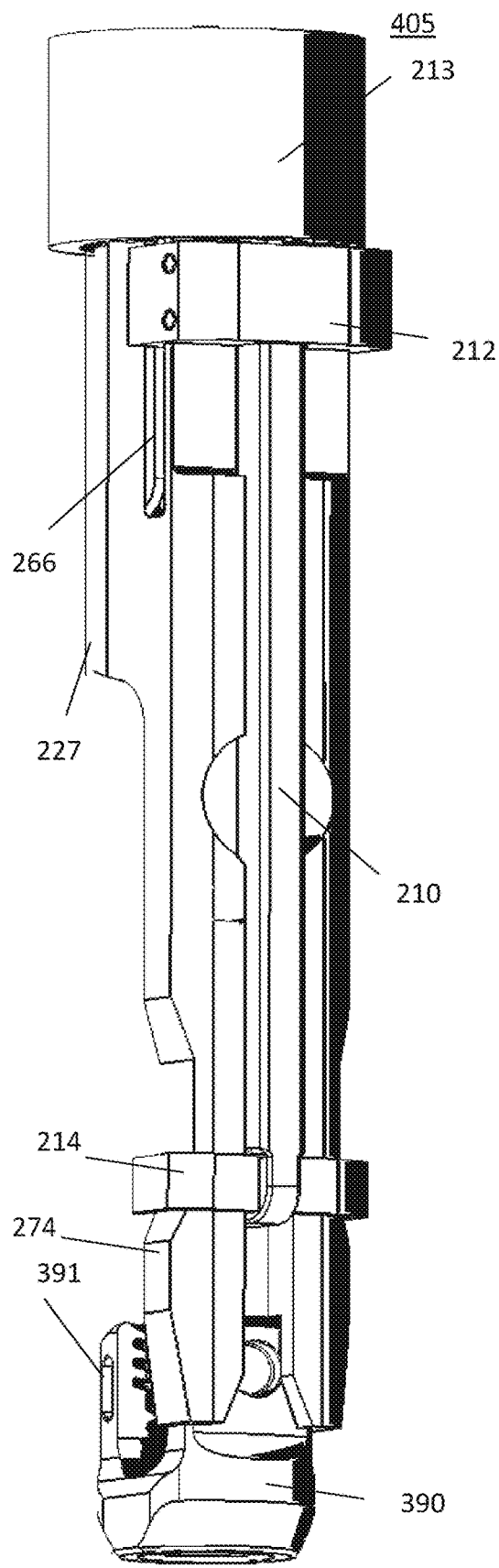
FIG. 4A is a perspective view of the universal instrument with the flexible prongs in an unlock state and a polyaxial head within the head cavity.
Figure 4B:
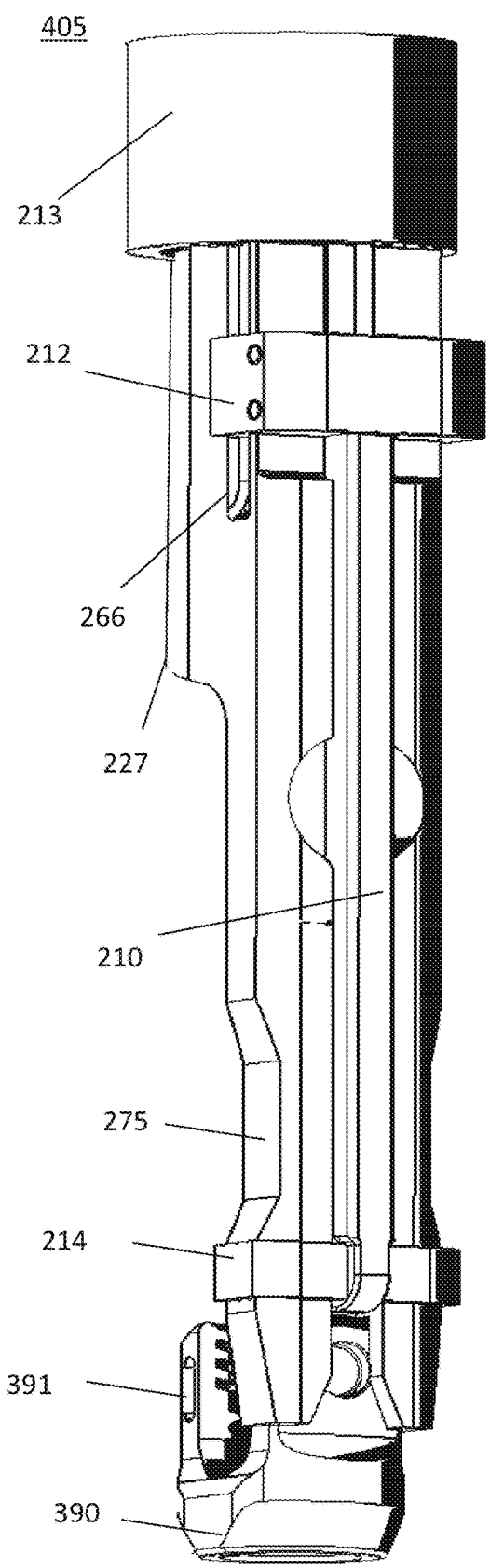
FIG. 4B is a perspective view of the universal instrument with the flexible prongs in a lock state and the polyaxial head locked within the head cavity.

The I-shaped clamp 210 may include a first position, as best seen in FIG. 4A. In the first position, the I-shaped clamp unclamps the flexible prongs 265A and 265B. Accordingly, the flexible prongs 265A and 265B are in an unlocked state and forced to separate via the wedge 233. In a second position, as best seen in FIG. 4B, the flexible prongs 265A and 265B are locked. Each flexible prong 265A and 265B may include a protrusion 279 to engage a corresponding slot 391 in the polyaxial head 390, as will be discussed in relation to FIGS. 4A-4B. The terms "first position" and "second position" are arbitrary and used as a frame of reference.

The I-shaped clamp 210 may slide from the second position to the first position to lock the flexible prongs 265A and 265B around the polyaxial head 390 such that protrusions 279 engage corresponding slots 391 in the polyaxial head 390 and become locked in position.

The elongated member 206 has a first side 221 and a second side 222 opposite the first side. The first side 221 includes the female attachment channel 207. The female attachment channel 207 includes a cuff member 227 with a front groove 229. The second side 222 includes side slide channels 266 configured to interface with clamp ends 256 of the first clamp member 212.

The first clamp member 212 may include a holding tab 217 extending away from the elongated member 206, the holding tab 217 being, for example, fixedly connected to the interconnecting bar 215. The holding tab 217 may include a top side 218 and a bottom side 219 such that applying a force to the bottom side of the holding tab 217 slides the I-shaped clamp 210 in the direction of the first end 246 to lift the second clamp member 214. Alternately, the sides or clamp ends 256 of the holding tab 217 may be used to slide the I-shaped clamp 210 up or down.

The prongs 265A and 265B are generally mirror images of each other. Therefore, only one prong will be described in detail. Each prong may include a lateral side 270 and a medial side 271. Each prong may include a first prong end 272 proximate the female attachment channel 207 and a second prong end 273 distal from the female attachment channel 207. Each prong may include a ridge 274, as best seen in FIGS. 3A-3B, between the first prong end 272 and the second prong end 273. Each prong may include a notch 275 formed in the lateral side 270 between the ridge 274 and the first prong end 272. Each prong may include a head seat portion 277 formed in a medial side 271. The protrusion 279 may be positioned within the seat portion 277 to engage a slot 391 in the polyaxial head 390. The seat portions 277 in the prongs 265A and 265B may be mirror images.

During operation, the surgeon has access to the holding tab 217 to apply a force to lock or unlock (clamp or unclamp) the prongs 265A and 265B, simultaneously, where the prongs 265A and 265B are clamped together.

If the surgeon slides the holding tab 217 upward or in the direction of arrow ARROW 1, the first clamp member 212 and the second clamp member 214 simultaneously move upward until the second clamp member 214 passes the ridge 274 completely and moves into the notches 275 in the prongs 265A and 265B. The notch 275 may be a depression in the lateral side of the prongs 265A and 265B. The depth of the depression allows the prongs 265A and 265B separate under the application of a separating force by the wedge 233. The contour of the medial side of the prongs 265A and 265B when side-by-side may form a plurality of gap portions of different gap widths.

FIG. 3A is a perspective view of the universal instrument 305 and a polyaxial head 390. The universal instrument 305 includes an upper collar 213. The rest of the universal instrument 305 is essentially the same. Thus, the same reference numerals as used in relation to FIGS. 2A-2C will be used. FIG. 3B is a partial view of the universal instrument 105 of along the plane 3B of FIG. 2B. The upper collar 213 is used to lock the other interchangeable instruments, such as instrument 155, in place while attached to the universal instrument 105. The upper collar 213 allows/prevents the ball detents (i.e., ball detents 216 of FIG. 7A) from engaging with apertures or holes 528 in the head locker instrument 155. A similar configuration may be used with other interchangeable instruments. In the locked state, the ball detents 216 are prevented from moving out due to surface or ridge 723 in FIG. 7B. In the open position, the ball detents 216 can move out, radially, into the apertures or holes 528, as best seen in FIG. 7D. The ball detents 216 of the collar 313 are biased with a spring to the locked position. To insert or remove an instrument, the collar would have to be pulled up, compressing the spring.

In FIG. 3A, the universal instrument 305 may be unlocked or unclamped such that the second clamp member 214 may be aligned with the notches 275 along the lateral side of the prongs 265A and 265B. The polyaxial head 390 in one embodiment may be affixed and locked in the head cavity 280 of the universal instrument 105 prior to inserting the polyaxial head 390 and universal instrument 105 through an incision of a patient, as will be discussed in more detail in relation to FIGS. 4A and 4B. The head cavity 280 is a recessed portion of the prongs defined by the side-by-side seat portions 277 of the prongs 265A and 265B.

The polyaxial head 390 may include a base 392 with a depending yoke 393 with first and second yoke elements diametrically opposing each other. The yoke elements 393A and 393B have an aperture 394. The center axis of the aperture 394 of each yoke element 393A and 393B may be axially aligned. An interior surface of each yoke element 393A and 393B may include threads 395. The base 392 may include an aperture (not shown) configured, for example, to receive a pedicle screw shaft. The aperture (not shown) has a center axis that may be orthogonal to the center axis of aperture 394. At least one yoke element 393A may include slots 391 on diametrically opposing side surfaces of the at least one yoke element 393 of the polyaxial head 390. In one embodiment, the yoke elements 393A and 393B are mirror images. Thus, yoke element 393B may also include slots 391.

The protrusions 279 may be positioned within the seat portions 277 to engage the slots 391 on one yoke element 393A or 393B of in the polyaxial head 390. The wedge 233 shown separating the prongs 265A and 265B, in FIG. 3B. The wedge 233 may in some embodiments, separate the prongs 265A and 265B a distance until the lateral side of the notch may be in contact with the interior surface of dependent sides 231 of the second clamp member 214.

Referring now to FIGS. 4A and 4B, the universal instrument 405 is essentially the same as universal instrument 305, thus similar reference numerals are used to refer to the same components. FIG. 4A is a perspective view of the universal instrument 405 with the flexible prongs 265A and 265B in an unlock state and a polyaxial head within the head cavity 280. In FIG. 4A, the second clamp member 214 is shown in the unlocked or unclamped position. The holding tab 217 is shown in an uppermost position. The sides of the holding tab 217, for example, may be gripped by fingers of the surgeon to slide the I-clamp to a locked state or clamped position. FIG. 4B is a perspective view of the universal instrument 405 with the flexible prongs 265A and 265B in a lock state and the polyaxial head locked within the head cavity 280.

Figure 5A:
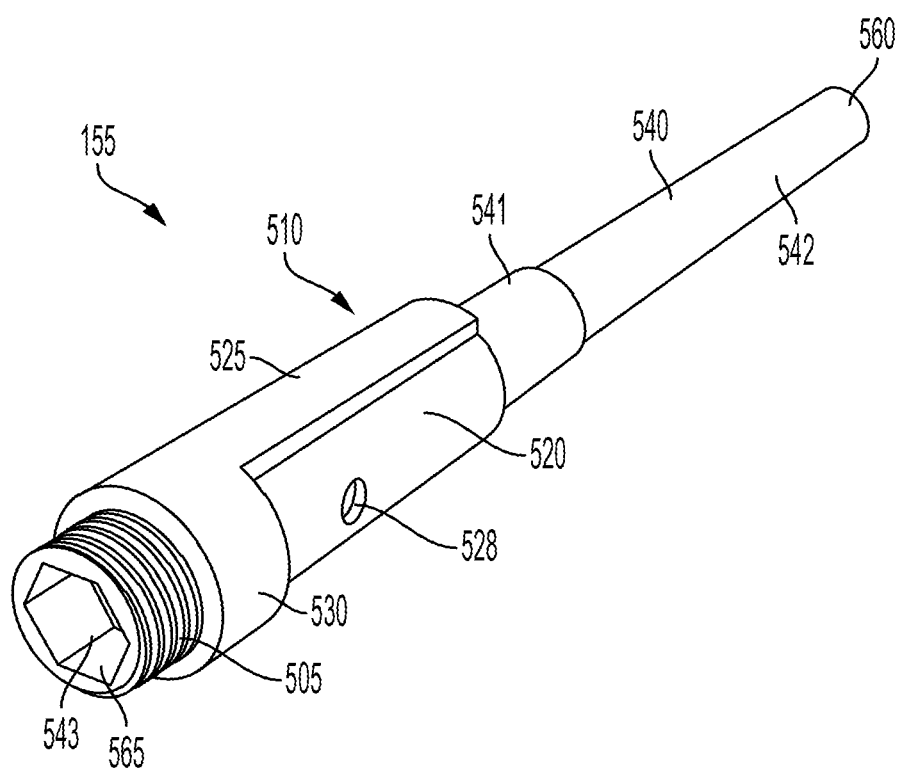
FIG. 5A is a top perspective view of a first interchangeable surgical instrument shown in FIG. 1.
Figure 5B:
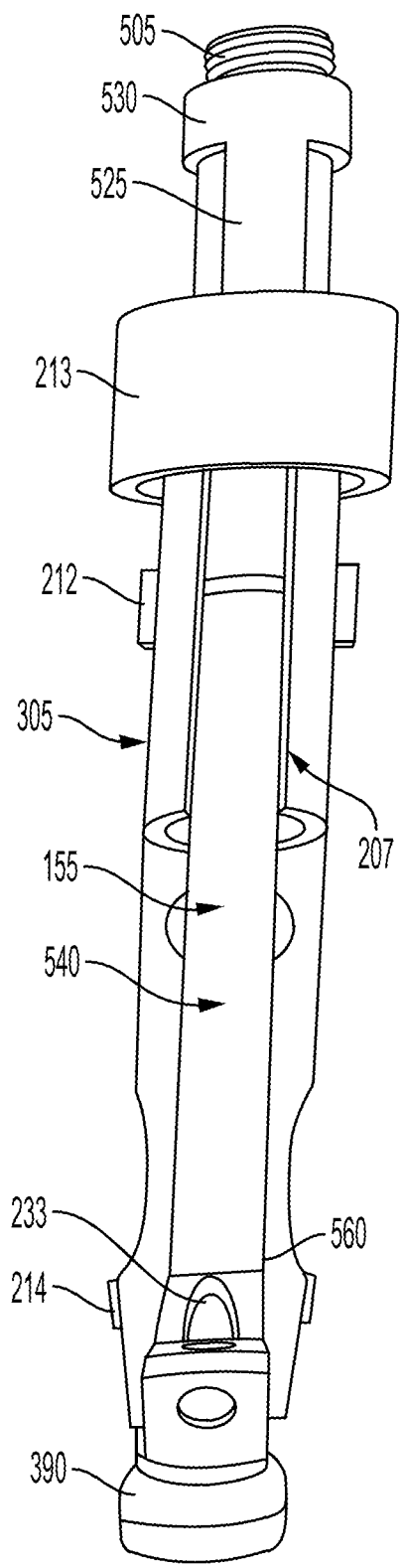
FIG. 5B is a front perspective view of the first interchangeable surgical instrument partly installed in the universal instrument.
Figure 6:
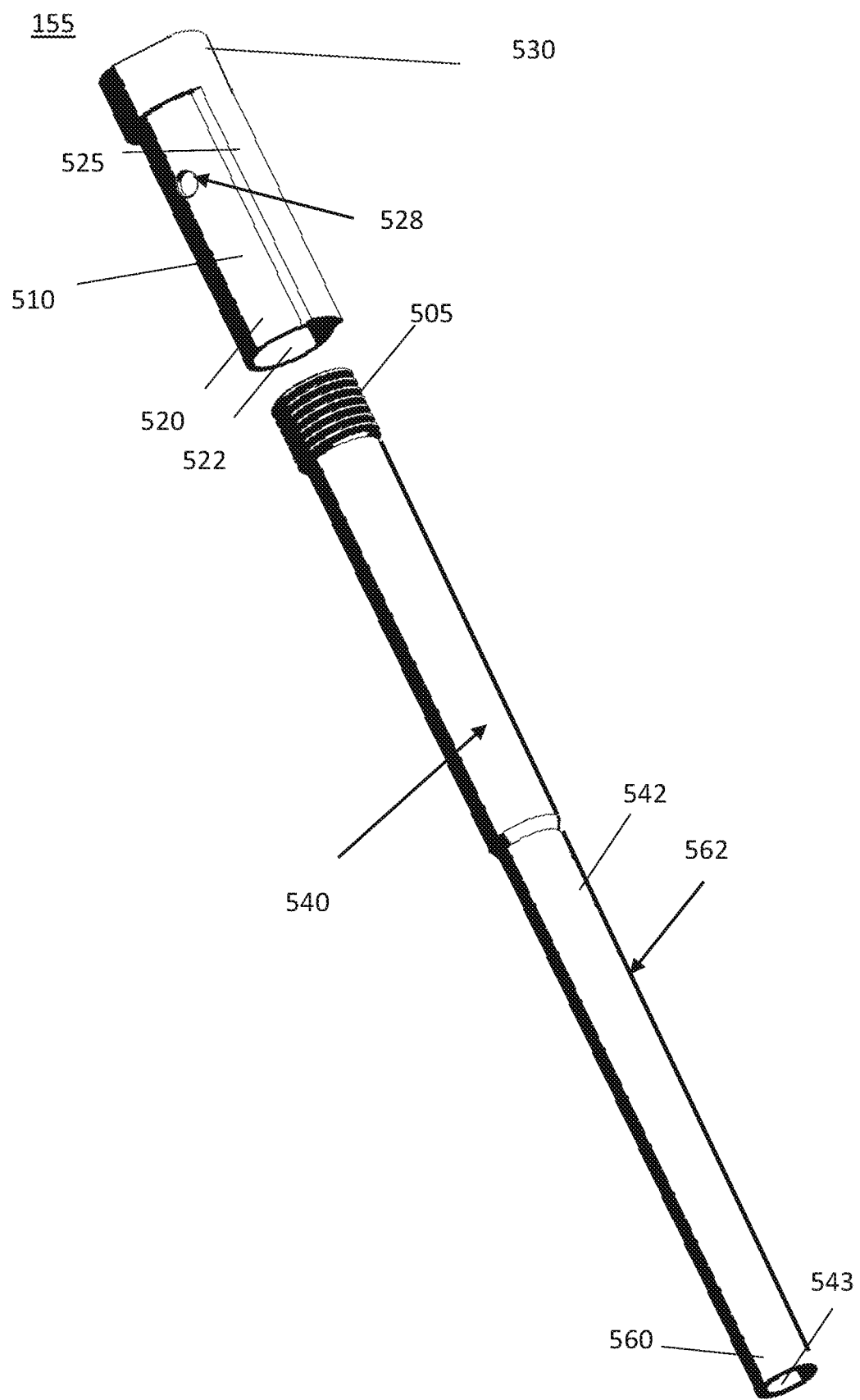
FIG. 6 is an exploded view of the components of the surgical instrument shown in FIG. 5A.

FIG. 5A is a top perspective view of a first interchangeable surgical instrument 155 shown in FIG. 1. FIG. 5B is a front perspective view of the first interchangeable surgical instrument partly installed in the universal instrument 305. FIG. 6 is an exploded view of the components of the surgical instrument shown in FIG. 5A. The instrument 155 may include a mated male attachment interface 510 that may be constructed and arranged to be received and secured in the female attachment channel 207 of a universal instruments 105 or 305. The male attachment interface 510 may include a first tubular member 520. The first tubular member 520 may include a hollow center 522, also denoted by the dashed lines 522 in FIGS. 7A-7D. The male attachment interface 510 may include a collar 530 integrated with the tongue 525. The collar 530 may provide a stop to prevent the male attachment interface 510 from sliding further down in collar 213.

The first tubular member 520 may include an outer diameter of the outer surface that is smaller than the inner diameter of the cuff member 227 of each universal instrument 305 (i.e., universal instrument 105). The first tubular member 520 may include a tongue 525 configured to be slid within and mated with the front groove 229 of a universal instruments 105, 305 as well as the collar 213. The first tubular member 520 may include diametrically opposing apertures or holes 528, as will be described in relation to FIGS. 7A-7D.

The instrument 155 may include a second tubular member 540 having a hollow center 543, also denoted by the dashed lines 543 in FIGS. 7A-7D. The second tubular member 540 may include a top internal hex element 565 in threaded cap 505 for pushing on the instrument such that the (lower) end 560 pushes on the crown of the polyaxial head to lock the head to the screw shank. The second tubular member 540 is dimensioned to fit within the hollow center of the first tubular member 520, as best seen in FIGS. 7A-7D. In some embodiments, the second tubular member 540 may include a first (upper) tubular section 541 with a first diameter and a second (lower) tubular section 542 having a second diameter smaller than the first diameter. In some embodiments, the second tubular member 540 may include only one diameter from the top distal end adjacent to threads on cap 505 to the bottom distal end (i.e., end 560).

The instrument 155 may include a threaded cap 505 configured as a knob at a first end of the second tubular member 540. The knob if turned in a first direction push on the crown 775 so that end 560 pushes the head on the shank of the screw 770. The end 560 may lock the polyaxial head to the screw shank.

Figure 7A:
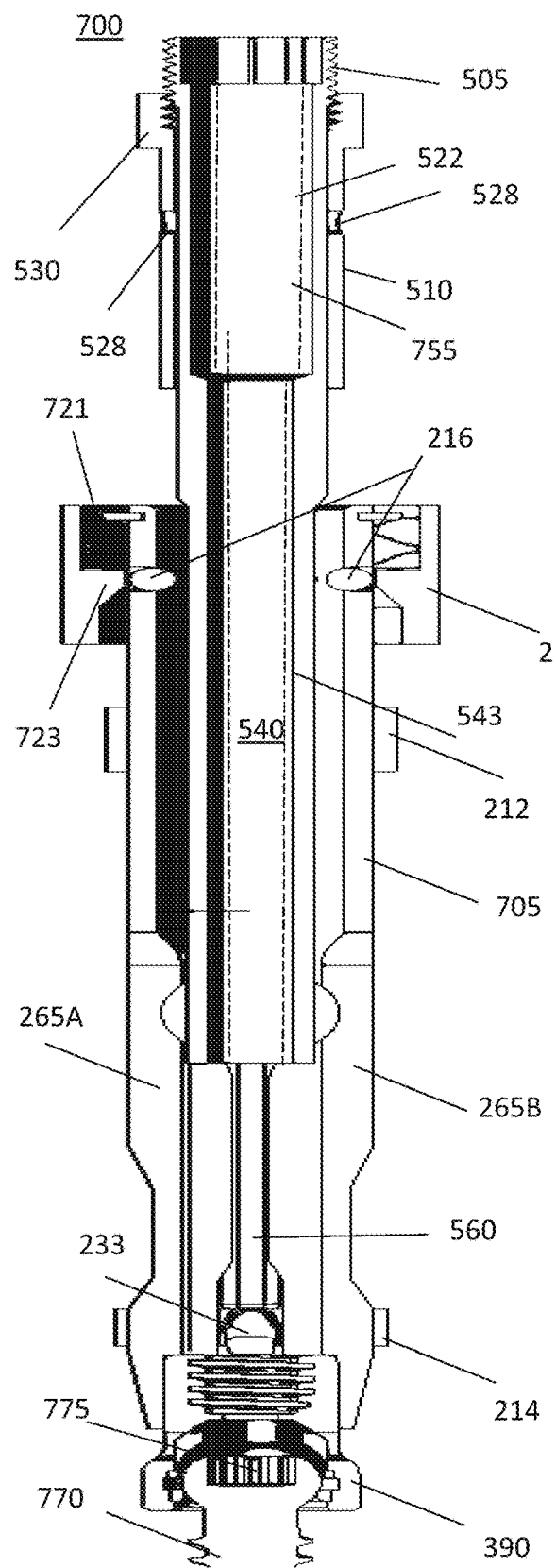
FIG. 7A is a cross-sectional view of a system with the universal instrument having a pedicle screw inserted and the first interchangeable surgical instrument at a first partially inserted position in the universal instrument with the crown driver member extended.

FIG. 7A is a cross-sectional view of a system 700 with a universal instrument 705 having a pedicle screw 770 inserted and the first interchangeable surgical instrument 755 at a first partially inserted position in the universal instrument 705. The cross-section of the upper collar 213 is shown connected to an upper end of the elongated member 206 above the cuff member 227. The upper collar 213 includes an upper interior seat 721. Two separate ball detents 216 are provided within the upper collar 213 and the elongated member 206. The crown 775 of the pedicle screw 770 is also inserted. The first interchangeable surgical instrument 755 (i.e., instrument 155) may be used as a crown driver which is configured to cause or produce a driving force to push the crown of the polyaxial head to lock the head to the screw shank. [BB1]

The interior of the collar 213 further includes a ridge 723 that is shown in a first position where the ridge 723 forces ball detents 216 to extend into the interior of the collar 213 just above the first end of the universal instrument 705. The ball detents 216 are in the path of the attachment interface 510.

Figure 7B:
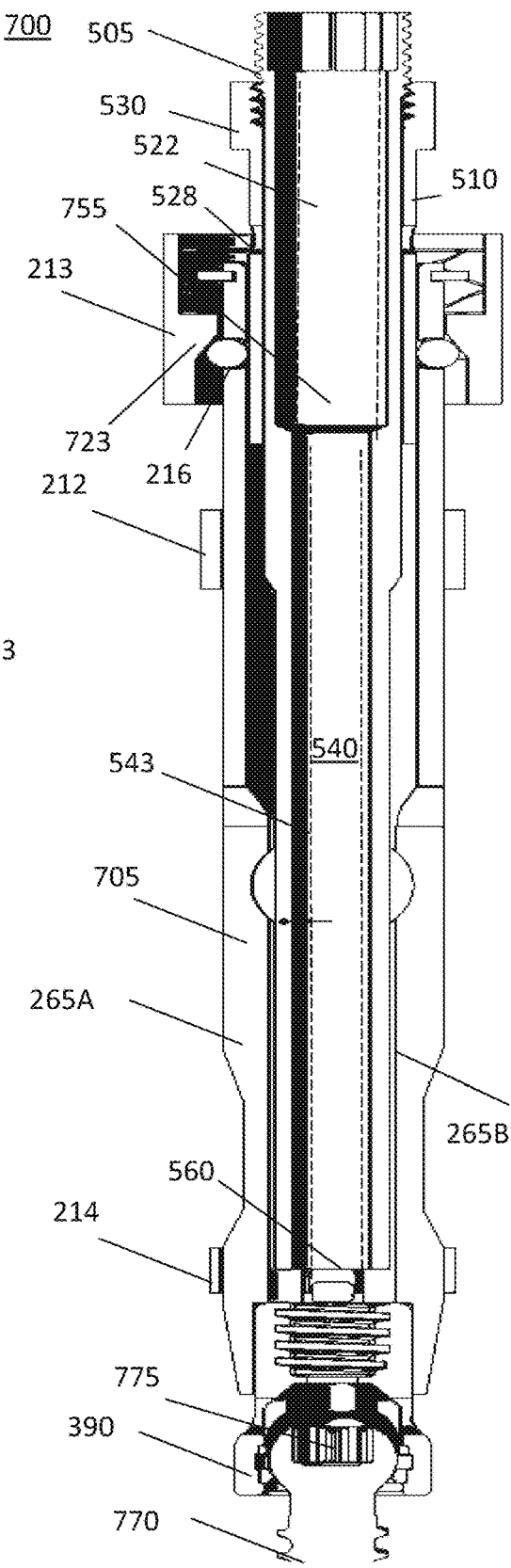
FIG. 7B is a cross-sectional view of a system of FIG. 7A with the universal instrument having a pedicle screw inserted and the first interchangeable surgical instrument at a second partially inserted position in the universal instrument.

FIG. 7B is a cross-sectional view of the system 700 of FIG. 7A with the universal instrument 705 having a pedicle screw 770 inserted and the first interchangeable surgical instrument 755 at a second partially inserted position in the universal instrument 705. The inserted position of the first interchangeable surgical instrument 755 may be achieved by applying downward pressure to the top of the threaded cap 505 (i.e., knob). The ridge 723 of the interior of the collar 213 is shown in a second position above the two detents 216. In FIG. 7A, the upper collar 213 is in the first position, and the instrument 755 would not be able to be fully locked. In FIG. 7B, the upper collar 213 is pulled up, allowing the force applied to the ball detents 216 by the ridge 723 to be removed or relaxed. Therefore, the instrument 755 can be slid into place and subsequently locked as shown in FIG. 7C.

Figure 7C:
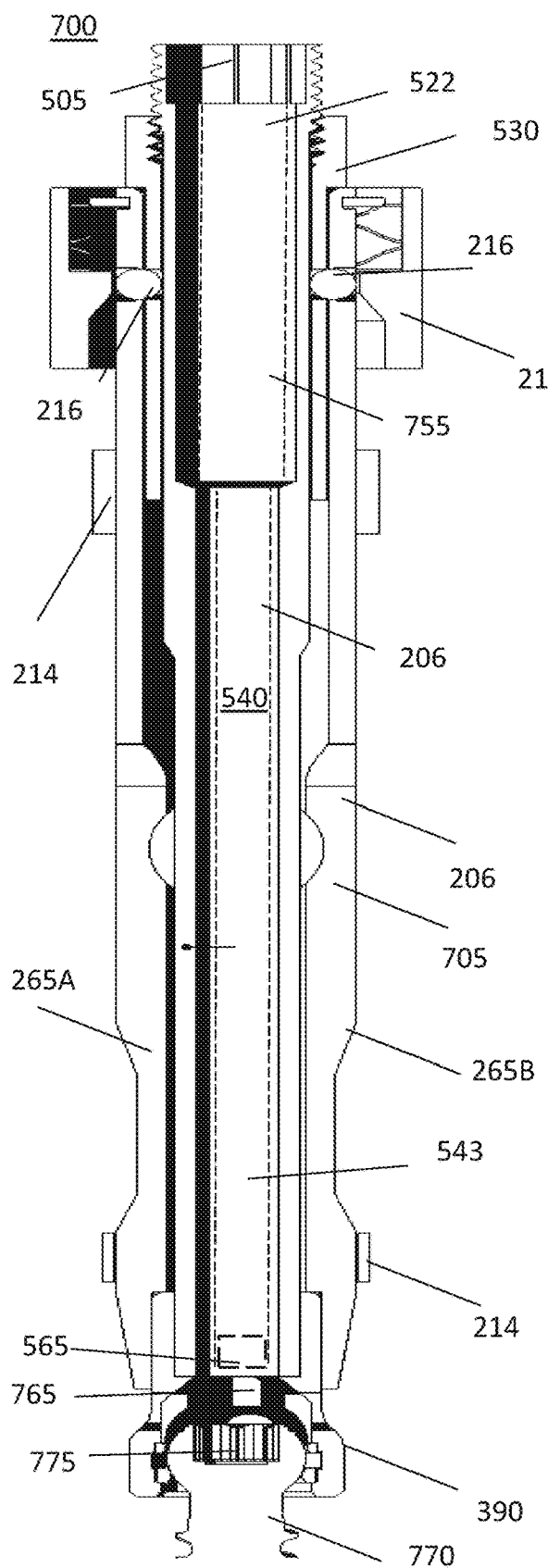
FIG. 7C is a cross-sectional view of a system of FIG. 7B with the universal instrument having the first interchangeable surgical instrument at a third partially inserted position in the universal instrument with the hex element in a first position.
Figure 7D:
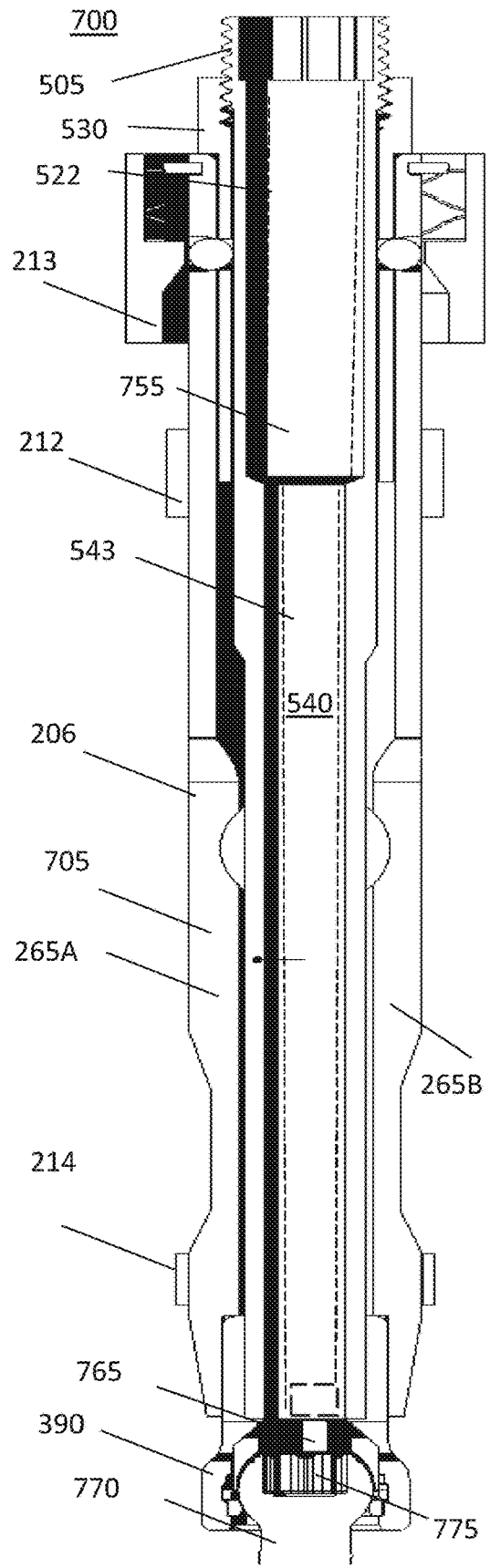
FIG. 7D is a cross-sectional view of a system of FIG. 7C with the universal instrument having the first interchangeable surgical instrument at a fourth partially inserted position in the universal instrument with the hex element turned to an intermediate position to push the crown of the polyaxial head.

FIG. 7C is a cross-sectional view of the system 700 of FIG. 7B with universal instrument 705 and the first interchangeable surgical instrument 755 at a third fully inserted position in the universal instrument 705 with the threaded cap 505 having a hex element 565 in a first position. The first position of the cap 505 corresponds to an unthreaded position. The ridge 723 of the interior of the collar 213 is shown slid back to its first position where the ridge 723 applies a force to the ball detents 216 to maintain the ball detents 216 in the apertures or holes 528. A tool (not shown) may be used to mate with the hex element 565 to turn the threaded cap 505. In other embodiments, the threaded cap 505 may include a knob to mate with the hex element 565 to rotate the threaded cap 505 in the collar 530.

FIG. 7D is a cross-sectional view of the system 700 of FIG. 7C with universal instrument 705 and the first interchangeable surgical instrument 755 at a fourth partially inserted position in the universal instrument 705. The threaded cap 505 has been turned to an intermediate position to push the pedicle screw crown 775. The collar 530 is shown abutting the top of the upper collar 213. The ridge 723 of the interior of the collar 213 is shown in the first position.

FIG. 8A is a cross-sectional view of the system 800 with the universal instrument 705 having the first interchangeable surgical instrument 755 at a fifth partially inserted position in the instrument 705 with the knob turned to an intermediate position to push the pedicle screw crown. The ridge 723 of the interior of the collar 213 is shown in the second position. Part of the collar 530 of the first interchangeable surgical instrument 755 is shown recessed in collar 213 of the universal instrument 705. The second position of the ridge 723 allows the force exerted by the ridge 723 to be removed. Consequently, the ball detents 216 can spring out of the apertures or holes 528 of head lock instrument 755 so that the head lock instrument 755 can be removed. The collar 530 is shown recessed in seat 721 and the ridge 723 above the ball detents 216.

FIG. 8B is a cross-sectional view of the system 800 of FIG. 8A with the universal instrument 705 having the first interchangeable surgical instrument being in a retracted position relative to the universal instrument 705 so that it can be removed.

Figures 9A, 9B:
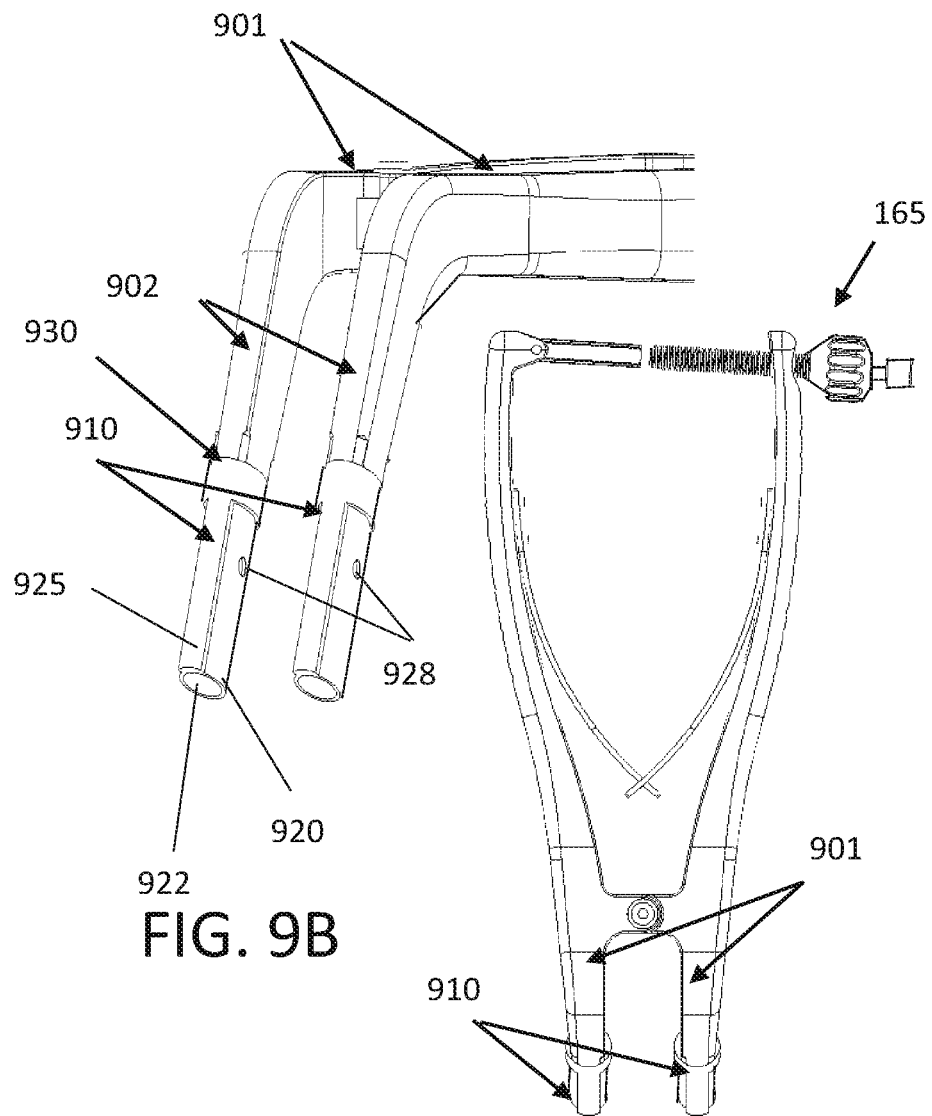
FIG. 9A is a front perspective view of a second surgical accessory.
FIG. 9B is a partial view of the second surgical accessory with mated male attachment interfaces.

FIG. 9A is a front perspective view of a second surgical accessory 165. FIG. 9B is a partial view of the second surgical accessory 165 with mated male attachment interfaces 910. The second surgical accessory 165 may include a compressor/distractor surgical instrument. The compressor/distractor surgical instrument 165 may include a pair of legs 901 each of which may include an attachment end 902. The each attachment end 902 may include a mated male attachment interface 910. The mated male attachment interface 910 may be constructed and arranged to be received and secured in the female attachment channel 207 of a pair of universal instruments 105, as best seen in FIG. 1. The male attachment interface 910 of each attachment end 902 may include a tubular member 920. The tubular member 920 may include a hollow center 922. The pair of attachment ends 902 of the pair of legs 901 may be angled and spaced apart at a distance that allows the male attachment interfaces 910 to be received in two adjacent universal instruments 105. The compressor/distractor surgical instrument 165 functions in a known manner thus no further discussion is necessary.

The tubular member 920 may include an outer diameter of the outer surface that is smaller than the inner diameter of the cuff member 227 (FIG. 2B) of each universal instrument 105. The tubular member 920 may include a tongue 925 configured to be slid within and mated with the front groove 229 (FIG. 2B) of a respective one of the universal instruments 105. Each tubular member 920 may include diametrically opposing apertures or holes 928. The aperture or holes 928 may be configured to receive ball detents 216 to lock the instrument 165 to the universal instruments 105 or 705, as previously described in relation to head locker instrument 155 or 755.

The pair of male attachment interfaces 910 are easily attached during surgery by sliding the male attachment interfaces 910 into two cuff members 227 (FIG. 2B) of two instruments 105, simultaneously. In other scenarios, each male attachment interface may be attached one at a time. Each male attachment interface 910 may include a collar 930 integrated with the tongue 925. The collar 930 may provide a stop to prevent the male attachment interface 910 from sliding further in the cuff member 227.

Figure 10:
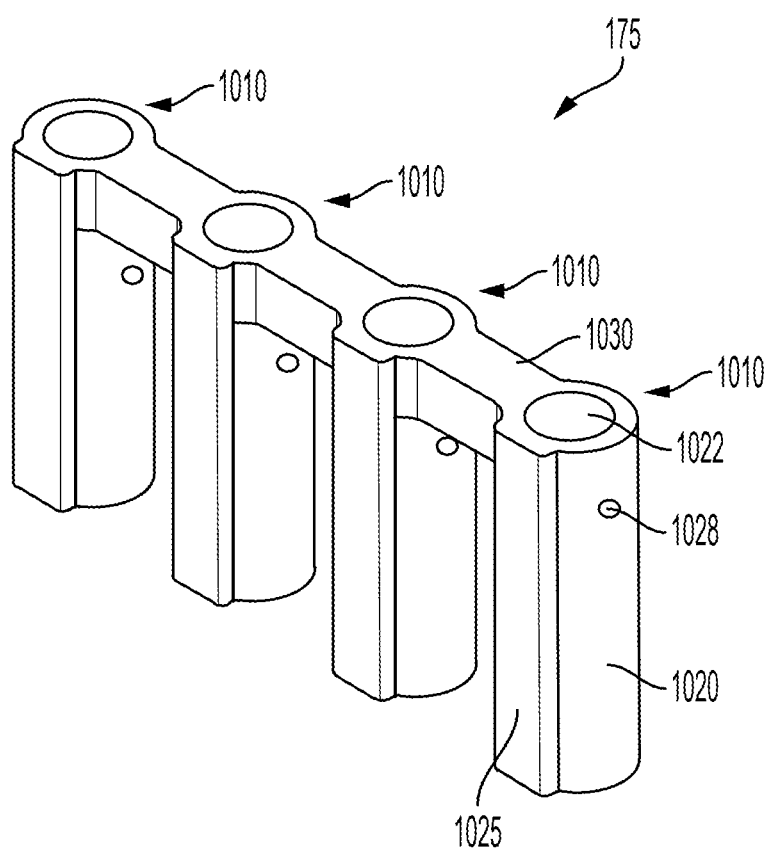
FIG. 10 is a perspective view of a third surgical accessory with mated male attachment interfaces.

FIG. 10 is a perspective view of a third surgical accessory 175 with mated male attachment interfaces. The third surgical instrument 175 may include a derotator crosslink instrument. The derotator crosslink instrument 175 may include a plurality of mated male attachment interfaces 1010, each of which may be constructed and arranged to be received and secured in the female attachment channel 207 of a plurality of universal instrument 105 arranged in series or space relation. In the illustration, the derotator crosslink instrument 175 may include 2 or more mated male attachment interfaces 1010. The illustrated example includes four mated male attachment interfaces 1010 arranged in series. Each male attachment interface 1010 may include a tubular member 1020. The tubular member 1020 may include a hollow center 1022. One or more of the tubular members 1020 may include diametrically opposing apertures or holes 1028. The aperture or holes 1028 may be configured to receive ball detents 216 to lock the instrument 175 to the universal instruments 105 or 705, as previously described in relation to head locker instrument 155 or 755. Adjacent tubular members 1020 may, for example, be linked to the next tubular member 1020 in a series by a linking bar 1030.

The tubular member 1120 may include an outer diameter of the outer surface that is smaller than the inner diameter of the cuff member 227 of a universal instrument 105, as best seen in FIG. 2B. The tubular member 1020 may include a tongue 1025 configured to be slid within and mated with the front groove 229 of a respective one of the plurality of universal instruments 105. The linking bar 1030 extending between tubular members 1020 may be used as a stop to prevent further sliding of the tubular members 1020 in their respective cuff members 227 of the universal instruments 105 (FIG. 1).

Figure 11A:
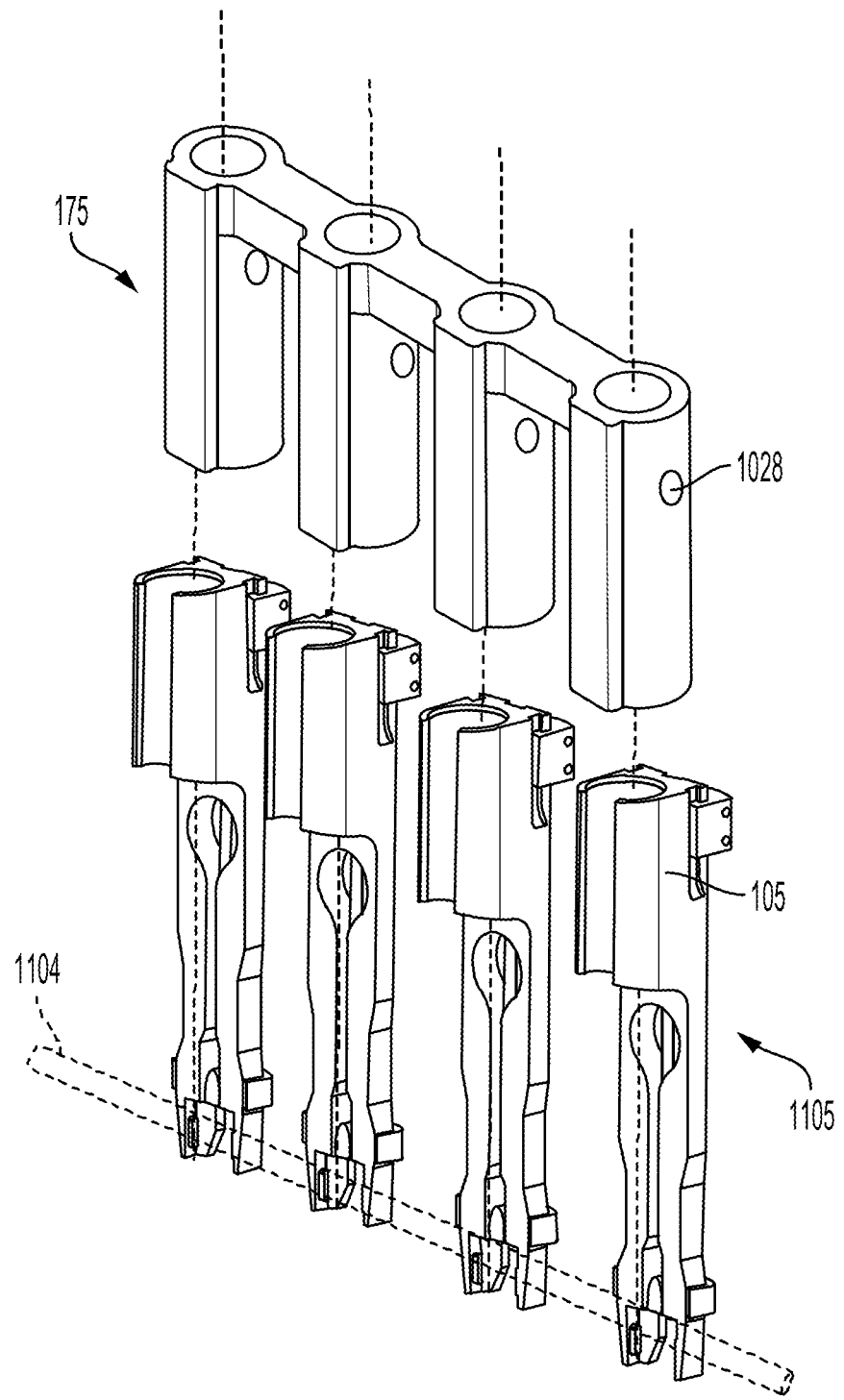
FIG. 11A is an exploded view of third surgical accessory with mated male attachment interfaces and a first set of universal instruments.

FIG. 11A is an exploded view of the third surgical accessory 175, as described in FIG. 10, with mated male attachment interfaces and a first set of universal instruments 1105. To prevent crowding of the drawing, the extension to first end 246 and collar 213 above the female attachment channel of the universal instrument 105 are not shown. The first set of universal instruments 1105 may include, for example, four universal instruments 105, as best seen in FIG. 1. Each universal instrument 105 may lock a polyaxial head 390 (FIG. 3A) through which a rod 1104, denoted in a dashed line, may link each of the universal instruments 105 to form the first set 1105. More or less universal instruments 105 may be linked together with rod 1104 on the same side of and along the spine. Each first set of universal instruments 1105 are arranged to link along the spine. In other words, each universal instrument 105 is associated with a different vertebrae.

Figure 11B:
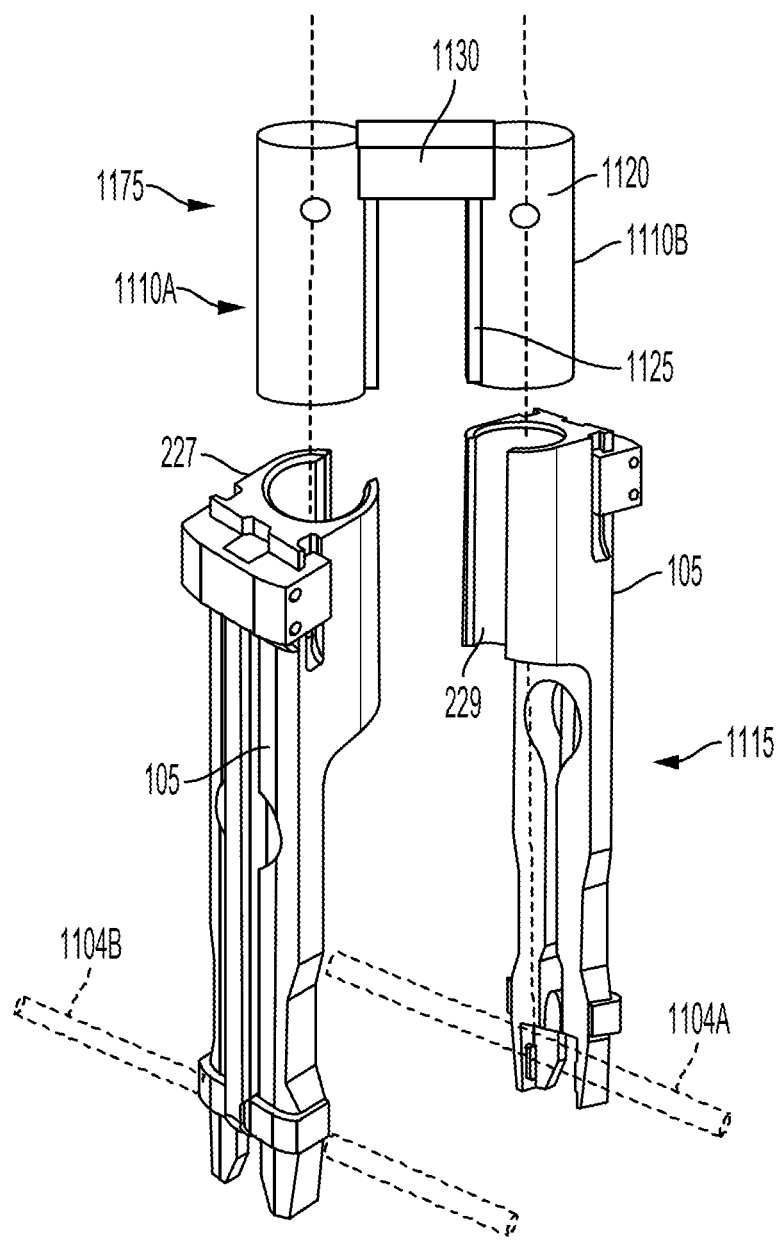
FIG. 11B is an exploded view of a fourth surgical accessory with mated male attachment interfaces and a second set of universal instruments.

FIG. 11B is an exploded view of a fourth surgical accessory 1175 with mated male attachment interfaces and a second set of universal instruments 1115. To prevent crowding of the drawing, the extension to first end 246 and collar 213 above the female attachment channel of the universal instrument 105 are not shown. The four surgical instrument 1175 may include two mated male attachment interfaces 1110A and 1110B which are mirror images of each other and diametrically opposing. The tubular member 1120 of each interface 1110A and 1110B may include a tongue 1125 configured to be slid within and mated with the front groove 229 of a respective one of the plurality of universal instruments 105. The linking bar 1130 extending between tubular members 1020 may be used as a stop to prevent further sliding of the tubular members 1120 in their respective cuff members 227 of the universal instruments 105. The mated attachment interfaces are illustrated as facing such that the tongues 1125 of each mated male attachment interface are facing each other. The rod 1104A may, for example, be attached to polyaxial heads on one side of the spine. The rod 1104B may, for example, be attached to polyaxial head on the other side of the spine. In the illustration, the fourth surgical accessory 1175 may be used to crosslink the universal instruments 105 used to lock polyaxial heads on each side of the same vertebrae.

In assembly, operation and use, a system 100, similar to the systems and methods described herein, is employed with a surgical procedure for treatment of a spinal disorder affecting a section of a spine of a patient, as discussed herein. For example, system 100 can be used with a surgical procedure for treatment of a condition or injury of an affected section of the spine including vertebrae. In some embodiments, one or all of the components of system 100 can be delivered as a pre-assembled device or can be assembled in situ. System 100 may be completely or partially revised, removed or replaced.

For example, system 100 can be employed with a surgical treatment of an applicable condition or injury of an affected section of a spinal column and adjacent areas within a body, such as, for example, vertebrae (not shown). In some embodiments, system 100 may be employed with one or a plurality of vertebra. To treat a selected section of the vertebrae, a medical practitioner obtains access to a surgical site including the vertebrae in any appropriate manner, such as through incision and retraction of tissues. In some embodiments, system 100 can be used in any existing surgical method or technique including open surgery, mini-open surgery, minimally invasive surgery including percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision may be made in the body of a patient and a cutting instrument (not shown) creates a surgical pathway for delivery of implantable components of system 100. A preparation instrument (not shown) can be employed to prepare tissue surfaces of vertebrae, as well as for aspiration and irrigation of a surgical region.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A universal surgical instrument comprising:
   an elongated member extending in a longitudinal direction between a first end and a second end, the second end having flexible prongs with a head cavity to hold therebetween a polyaxial head;
   a cuff member disposed adjacent the first end and being configured to interface with interchangeable surgical instruments, the cuff member defining an attachment channel extending in the longitudinal direction between a first opening and a second opening, wherein a sidewall of the cuff member comprises a third opening extending in the longitudinal direction between the first opening and the second opening; and
   an I-shaped clamp coupled to the elongated member and being configured to unlock and separate the flexible prongs to expand the head cavity for placement of the polyaxial head therein and to lock the head cavity in response to application of a force to slide the I-shaped clamp along the elongated member to a locked position.

2. The instrument according to claim 1, wherein the I-shaped clamp comprises:
   a first clamp member slidably coupled to the first end;
   a second clamp member slidably coupled to the second end; and
   an interconnecting bar interconnecting the first clamp member to the second clamp member, and wherein in the locked position of the I-shaped clamp, the second clamp member clamps the flexible prongs and in an unlocked position the second clamp member unclamps the flexible prongs.

3. The instrument according to claim 2, wherein the I-shaped clamp further comprises:
   a wedge coupled to the second clamp member at a location between the flexible prongs so that as the I-shaped clamp is slid from the locked position to the unlocked position, the flexible prongs expand by application of a force by the wedge to a medial side of each flexible prong.

4. The instrument according to claim 2, wherein:
   the first clamp member includes a holding tab extending away from a second side of the elongated member; and
   the holding tab being fixedly connected to the interconnecting bar and applying the force to the holding tab slides the I-shaped clamp in the direction of the first end to lift the second clamp member and unclamp the flexible prongs.

5. The instrument according to claim 1, wherein:
   the elongated member has a first outside side surface and a second outside side surface opposite the first side;
   the first outside side surface includes the cuff member; and
   the second outside side surface includes slide channels configured to interface with an upper portion of the I-shaped clamp, the slide channels being exposed.

6. The instrument according to claim 1, wherein the flexible prongs comprises a first prong and a second prong, each prong comprises:
   a lateral side;
   a medial side;
   a first prong end proximate the cuff member;
   a second prong end distal from the cuff member;
   a ridge between the first prong end and the second prong end;
   a notch formed in the lateral side between the ridge and the first end;
   a head seat portion formed in the medial side; and
   a protrusion positioned within the head seat portion to engage a slot in the head.

7. The instrument according to claim 1, wherein:
   each flexible prong comprises a protrusion to engage a corresponding slot in the polyaxial head; and
   the locked position of the I-shaped clamp causes the protrusion to be locked in the corresponding slot of each flexible prong.

8. A surgical instrument system comprising:
   at least one universal surgical instrument, each universal surgical instrument comprising:
   an elongated member extending in a longitudinal direction between a first end and a second end, the second end having flexible prongs with a head cavity to hold therebetween a polyaxial head,
   a female attachment channel disposed adjacent the first end, the female attachment channel extending in the longitudinal direction between a first opening and a second opening, wherein a third opening extends in the longitudinal direction between the first opening and the second opening, and
   an I-shaped clamp coupled to the elongated member and being configured to unlock and separate the flexible prongs to expand the head cavity for placement of the polyaxial head therein and to lock the head cavity in response to application of a force to slide the I-shaped clamp along the elongated member to a locked position; and
   at least one interchangeable surgical instrument, each interchangeable surgical instrument including a male attachment interface configured to mate with the female attachment channel, wherein the male interface prevents rotation of the at least one interchangeable instrument within the female attachment channel.

9. The system according to claim 8, wherein the at least one universal surgical instrument comprises a plurality of universal surgical instruments.

10. The system according to claim 9, wherein the at least one interchangeable surgical instrument comprises a head locker instrument for attachment of a pedicle screw crown.

11. The system according to claim 9, the at least one interchangeable surgical instrument comprises a compressor/distractor surgical instrument.

12. The system according to claim 9, wherein the at least one interchangeable surgical instrument comprises a cross-link instrument to fasten together the plurality of universal surgical instruments or a set of universal surgical instruments of the plurality of universal surgical instruments.

13. The system according to claim 12, wherein the cross-link instrument comprises a plurality of male attachment interfaces to mate with the female attachment channel of the plurality of universal surgical instruments.

14. The system according to claim 8, wherein:
- the female attachment channel comprises an elongated C shaped cuff member; and
- the male interface comprises a tubular member and a tongue along an exterior of the tubular member, the tubular member configured to fit within the cuff member such that the tongue is non- rotatably disposed within the third opening.

* * * * *